(12) United States Patent
Nishiyama

(10) Patent No.: US 8,323,303 B2
(45) Date of Patent: Dec. 4, 2012

(54) LANCING DEVICE

(75) Inventor: Hisashi Nishiyama, Kyoto (JP)

(73) Assignee: Arkray, Inc., Kyoto (JP)

( * ) Notice: Subject to any disclaimer, the term of this patent is extended or adjusted under 35 U.S.C. 154(b) by 267 days.

(21) Appl. No.: 12/734,666

(22) PCT Filed: Nov. 15, 2008

(86) PCT No.: PCT/JP2008/070823
§ 371 (c)(1),
(2), (4) Date: May 14, 2010

(87) PCT Pub. No.: WO2009/063999
PCT Pub. Date: May 22, 2009

(65) Prior Publication Data
US 2010/0241149 A1 Sep. 23, 2010

(30) Foreign Application Priority Data
Nov. 16, 2007 (JP) ................ 2007-297939

(51) Int. Cl.
*A61B 5/151* (2006.01)
(52) U.S. Cl. ...................... 606/182; 606/181
(58) Field of Classification Search .......... 606/181, 606/182, 185; 604/156, 157
See application file for complete search history.

(56) References Cited

U.S. PATENT DOCUMENTS

| 6,197,040 B1 * | 3/2001 | LeVaughn et al. ............ 606/182 |
| 2006/0200181 A1 | 9/2006 | Fukazawa et al. |
| 2006/0247670 A1 * | 11/2006 | LeVaughn et al. ............ 606/181 |

FOREIGN PATENT DOCUMENTS

| JP | 2000-262498 A | 9/2000 |
| JP | 2005-342324 A | 12/2005 |
| JP | 2006-314718 A | 11/2006 |
| WO | WO 2004/091401 A1 | 10/2004 |

OTHER PUBLICATIONS

International Search Report mailed on Dec. 9, 2008.

* cited by examiner

*Primary Examiner* — Kathleen Sonnett
*Assistant Examiner* — Sarah Webb
(74) *Attorney, Agent, or Firm* — Rader, Fishman & Grauer PLLC

(57) ABSTRACT

By moving a control member 3 in a predetermined direction from a wait position, a lancing device A can perform a lancet retreat operation for retreating a lancet holder 2 to locate a lancet 9 at a predetermined retreated position and a lancet detachment operation for pushing out the lancet 9 forward of the lancet holder 2 after a lancing operation. The control member 3 returns to the wait position by action of a return member 7 both after the lancet retreat operation and after the lancet detachment operation. Thus, the lancing device A is convenient.

10 Claims, 12 Drawing Sheets

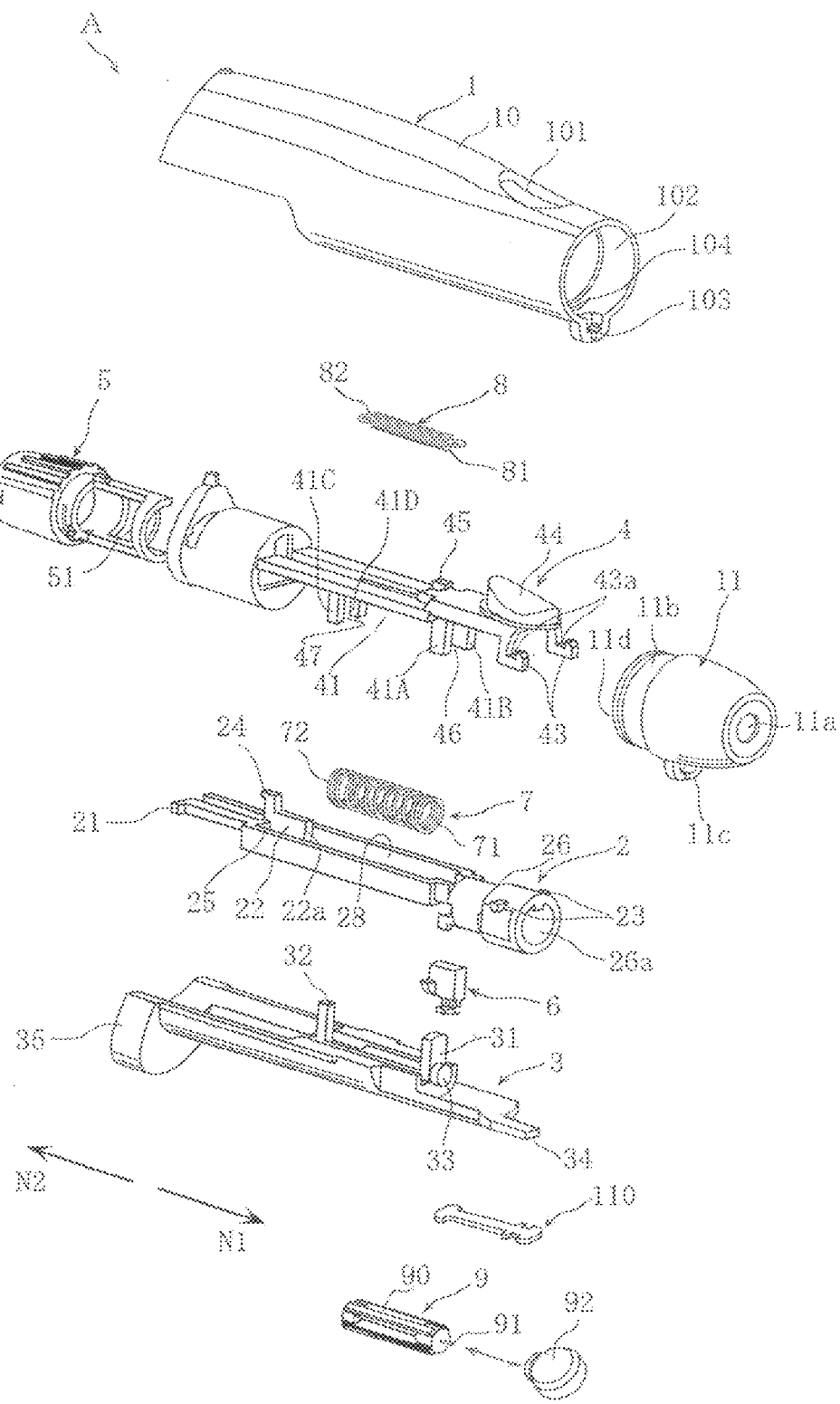

FIG. 4
FIG. 4A
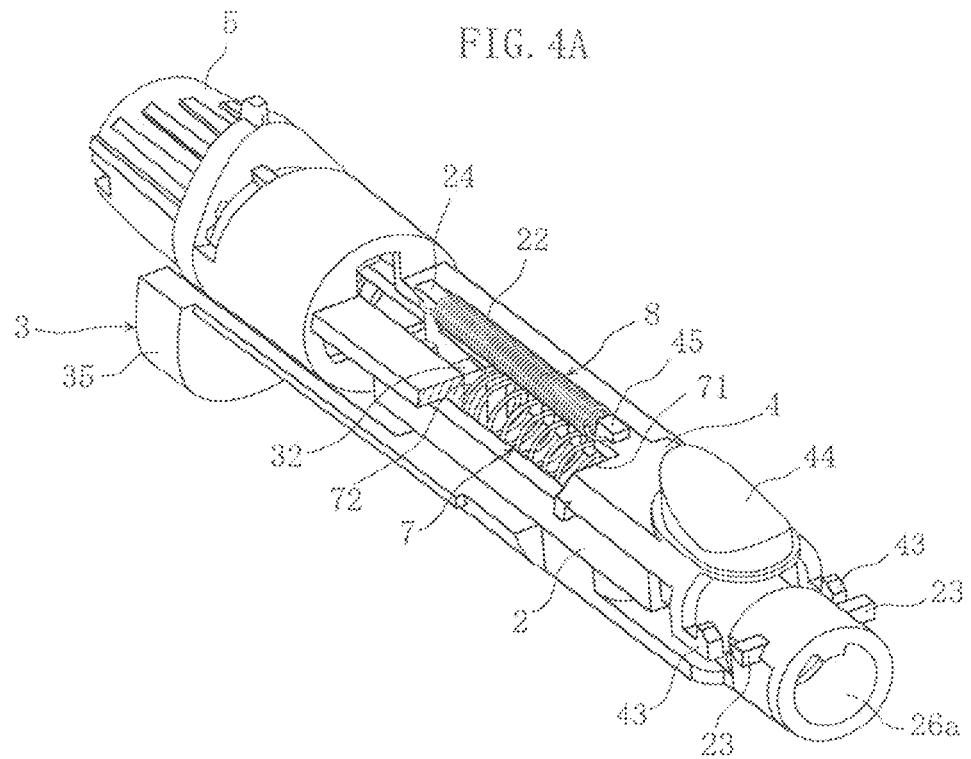
FIG. 4B
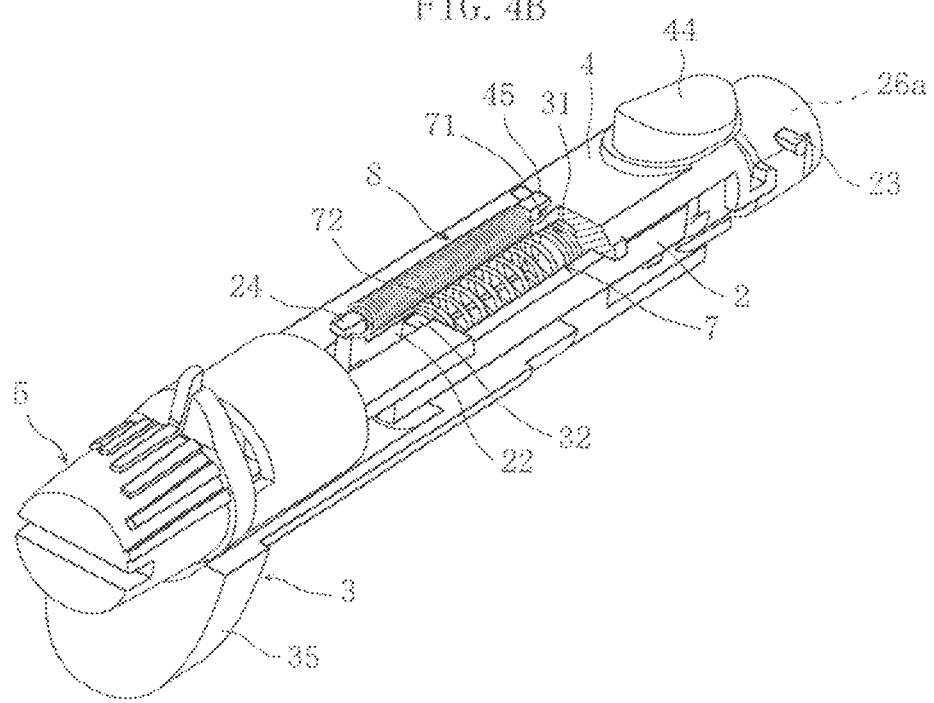

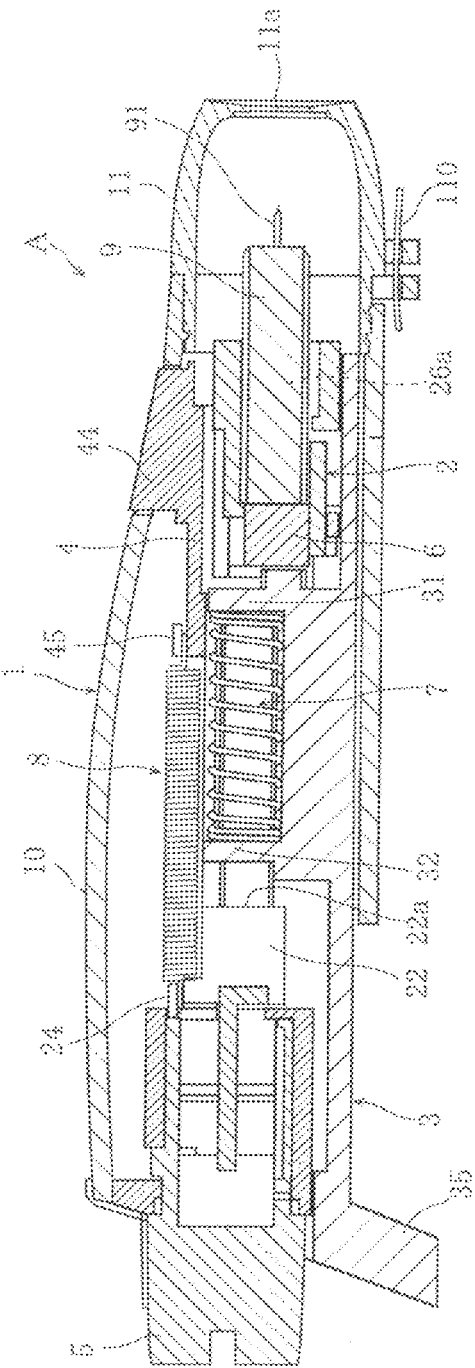
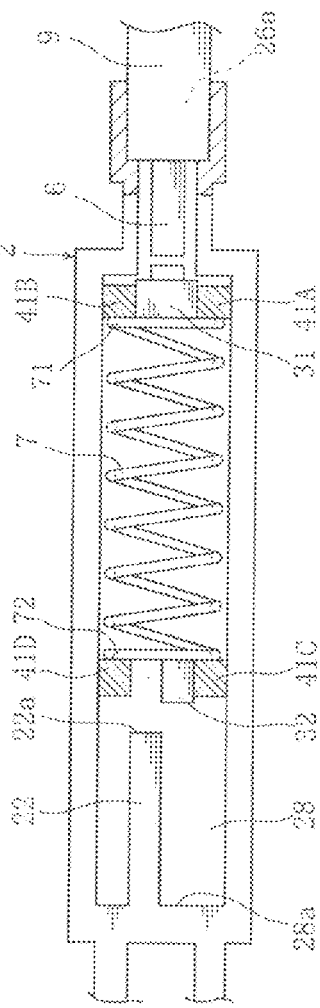

FIG. 7
FIG. 7A
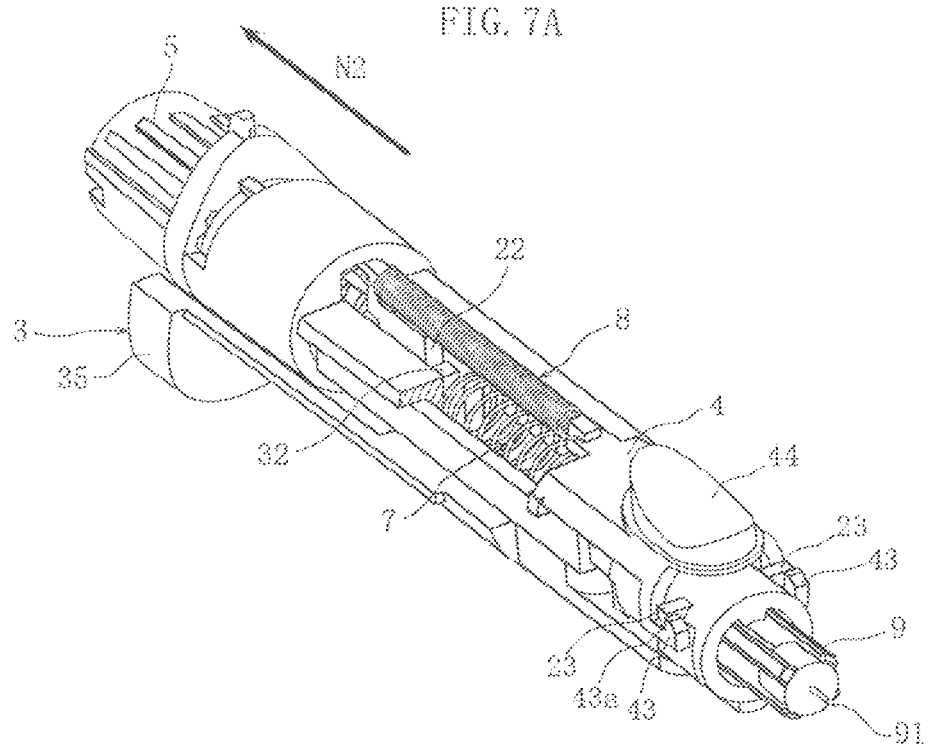
FIG. 7B
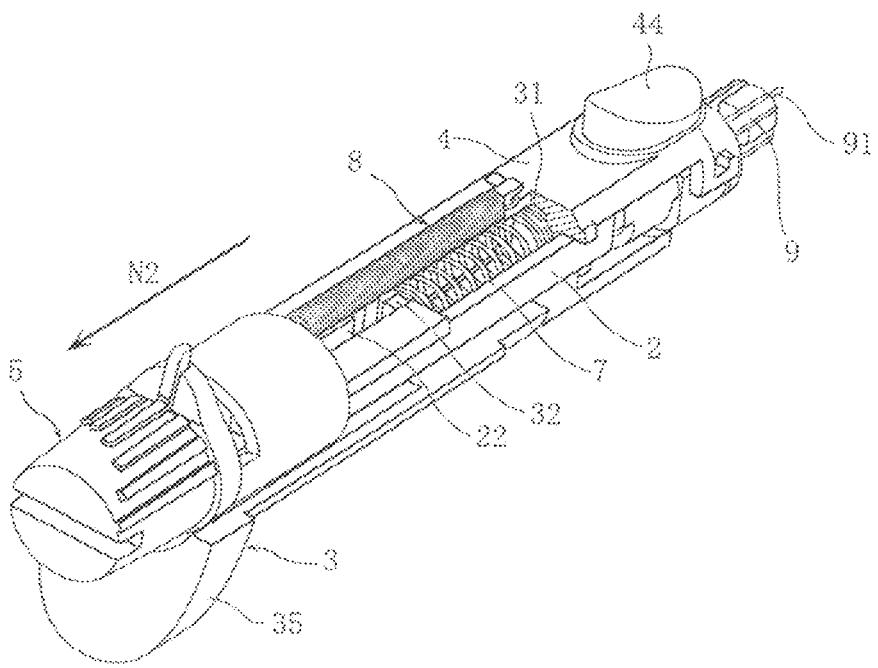

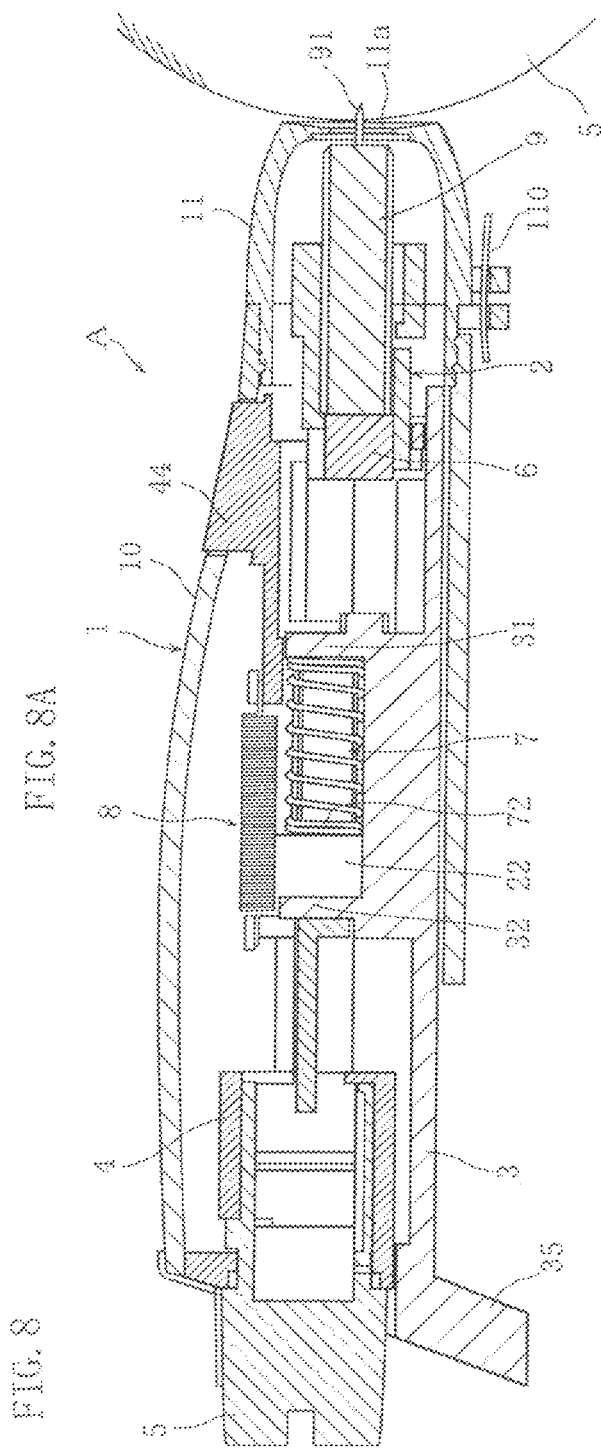
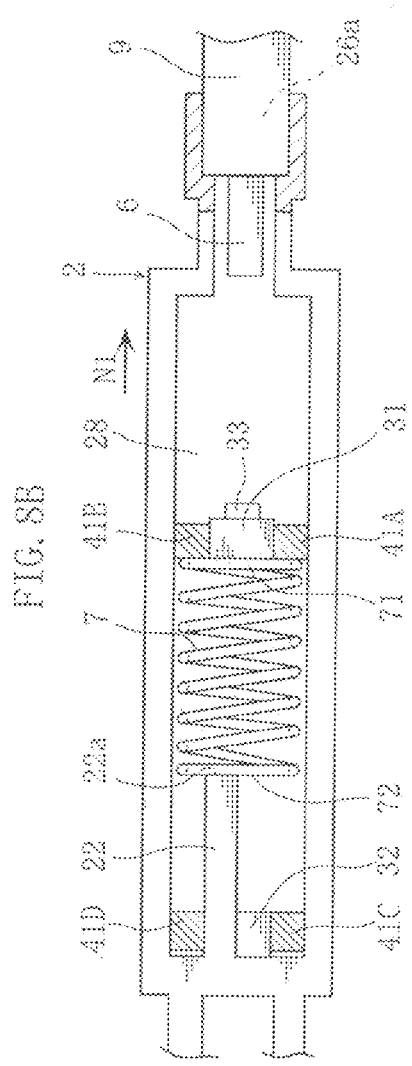

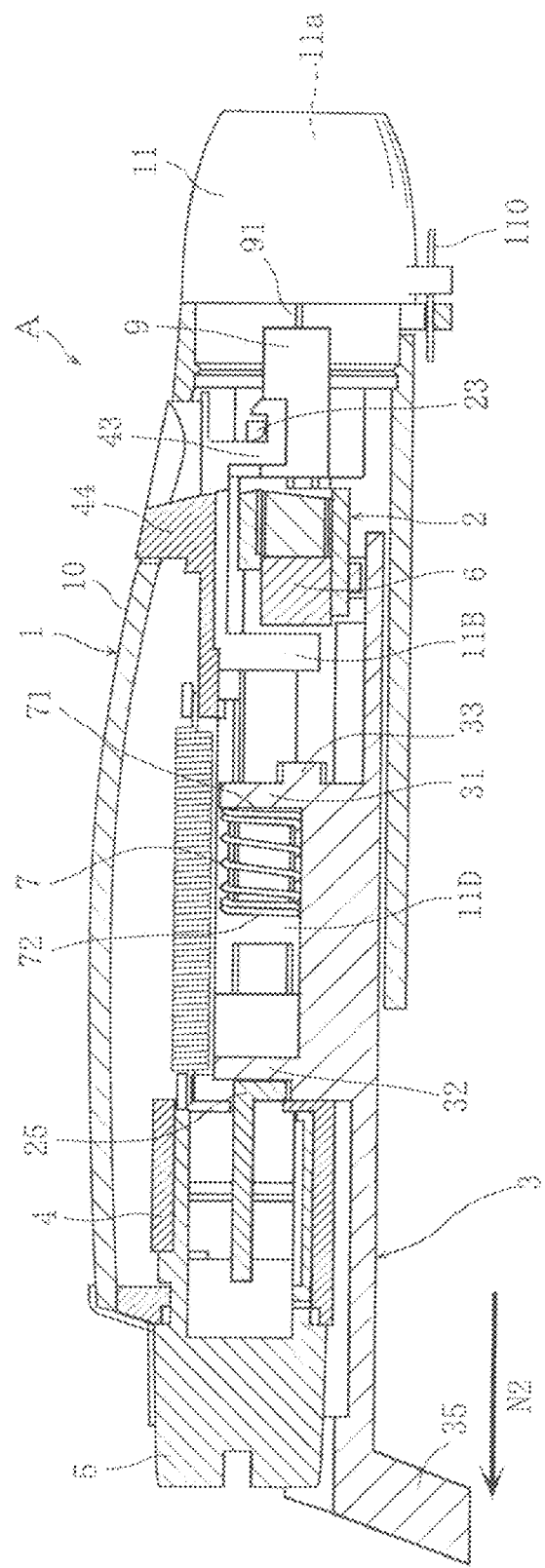
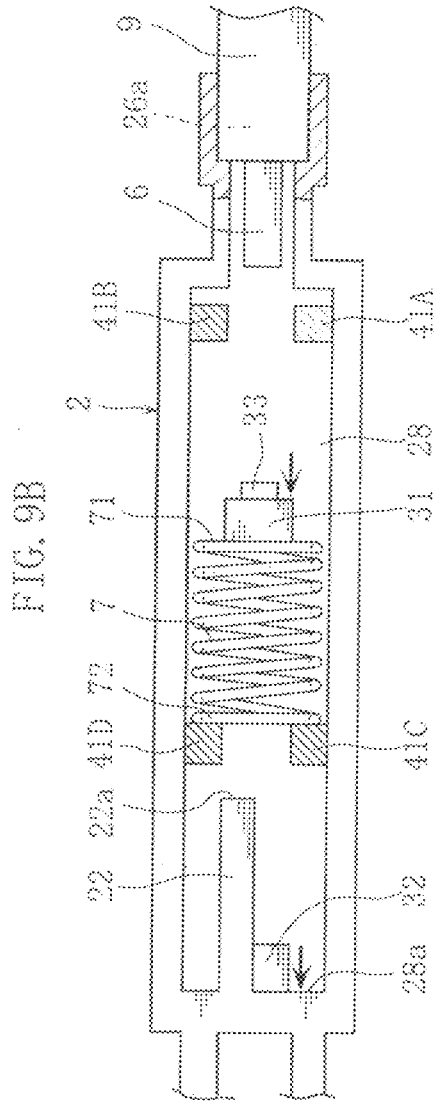

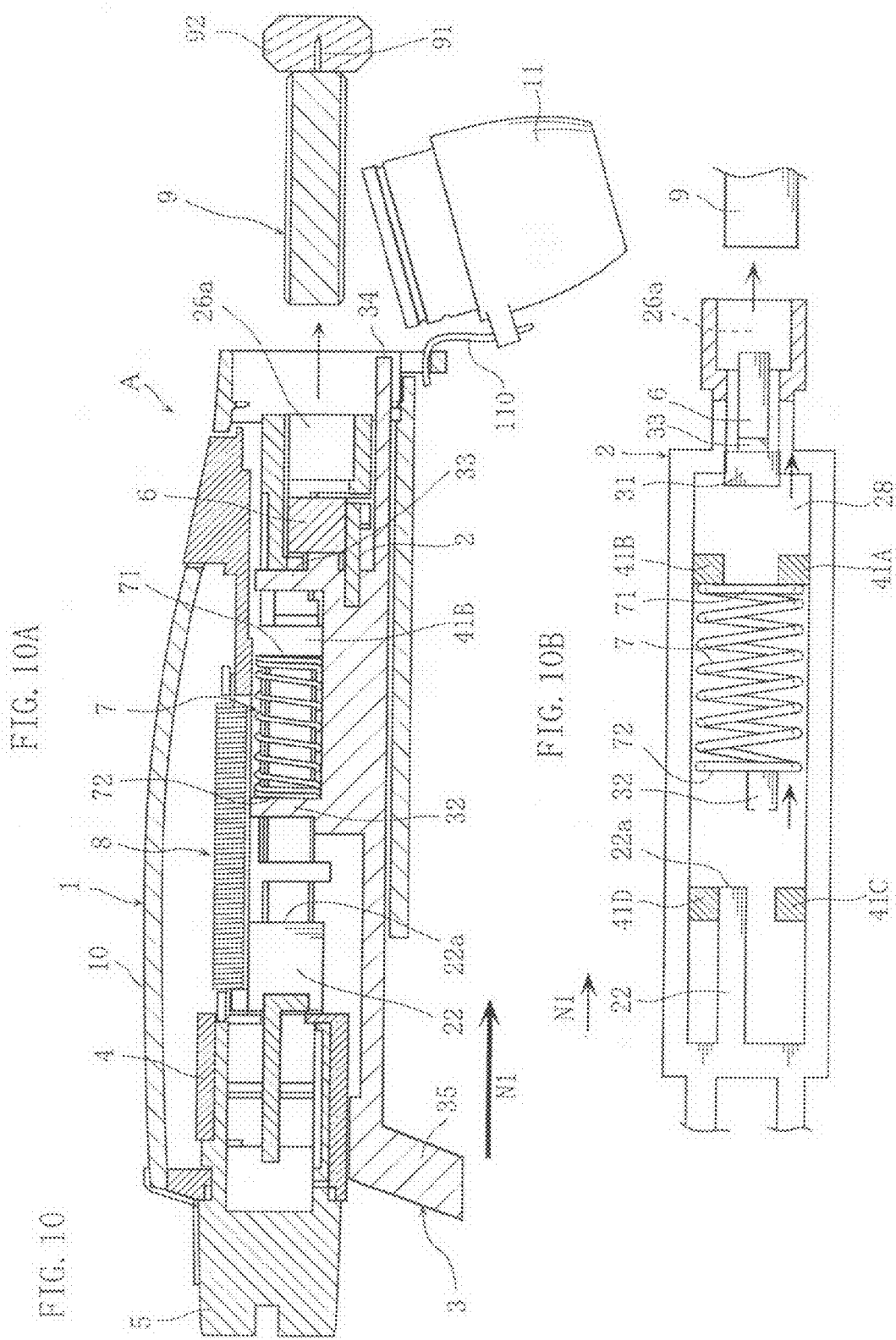

LANCING DEVICE

BACKGROUND OF THE INVENTION (1) Field of the Invention

The present invention relates to a lancing device for pricking skin with a tip end of a lancet to take blood or other body fluid or tissue for testing.

(2) Description of Related Art

FIG. 12 illustrates an example of conventional lancing device disclosed in Patent Document 1. In the lancing device B illustrated in the figure, a control member 230 including a control portion 230a, a lancet holder 220, an advance spring 280 and a return spring 270 are accommodated in a housing 210. When the control member 230 is retreated in the arrow Rr direction by handling the control portion 230a, the lancet holder 220 also retreats, compressing the advance spring 280. Thereafter, by using the resilient force of the advance spring 280, the lancet holder 220 quickly advances in the arrow Fr direction so that the needle 290a of the lancet 290 pricks a lancing target portion (not shown). In this way, the lancing target portion is caused to bleed, and blood can be taken from this portion for testing. The return spring 270 functions to return the control member 230 to its original wait position after the above-described operation is performed. Further, when the control member 230 is moved forward with the cap 240 of the housing 210 removed, the front end 233 of the control member 230 pushes the lancet 290 forward for detachment from the lancet holder 220. In this way, the lancet 290 after use is easily removed.

However, in the above-described lancing device B, after the control member 230 is advanced to detach the used lancet 290 from the lancet holder 220, the control member 230 does not automatically return to the original wait position. Thus, the user needs to operate the control portion 230a to return the control member 230 to the original wait position, which is troublesome. As a means to solve this problem, it may be considered to provide an additional return spring to retreat the control member 230 after it is advanced to detach the lancet 290 from the lancet holder 220. However, to employ this means leads to increase in number of parts, complicated structure, and increase in size of the lancing device and manufacturing cost.

Patent Document 1: JP-A-2000-262498

DETAILED DESCRIPTION OF THE INVENTION

An object of the present invention is to provide a lancing device which is capable of properly eliminating or lessening the above-described problems.

Means for Solving the Problems

To solve the above-described problems, the present invention takes the following technical measures.

SUMMARY OF THE INVENTION

According to the present invention, there is provided a lancing device comprising: a housing including an opening at a front end thereof; a lancet holder for holding a lancet within the housing, the lancet holder being movable in a back and forth direction of the housing to be able to advance the lancet toward the opening from a retreated position spaced from the opening; a control member which is movable from a predetermined wait position in a first and a second directions, movement of the control member in the second direction from the wait position enabling a lancet retreat operation for retreating the lancet holder to locate the lancet at the retreated position, movement of the control member in the first direction from the wait position enabling a lancet detachment operation for pushing out the lancet forward of the lancet holder; and a return member for returning the control member to the wait position after the lancet retreat operation is performed and returning the control member to the wait position after the lancet detachment operation is performed.

Preferably, the return member further functions to retreat the lancet holder after the lancet has advanced and pricked a lancing target portion.

Preferably, the return member includes a resilient member.

Preferably, the resilient member is a compression spring.

Preferably, the lancing device according to the present invention further comprises a front and a rear stoppers provided in the housing in contact with a front end and a rear end of the return member to restrict movement of the front end and the rear end in a back and forth direction; and a first and a second engagement portions provided at the control member and positioned to sandwich the return member in the back and forth direction. During the lancet retreat operation, the first engagement portion retreats to compress the return member between the first engagement portion and the rear stopper so that the return member pushes the first engagement portion forward after the lancet retreat operation. During the lancet detachment operation, the second engagement portion advances to compress the return member between the second engagement portion and the front stopper so that the return member pushes the second engagement portion backward after the lancet detachment operation.

Preferably, one of the front stopper and the first engagement portion is formed with an opening to avoid contact with the other one, and the opening has a width in a direction crossing the back and forth direction. Further, one of the rear stopper and the second engagement portion is formed with an opening to avoid contact with the other one, and the opening has a width in a direction crossing the back and forth direction.

Preferably, the first and the second engagement portions are projections projecting from the control member toward the return member. Part of the lancet holder is positioned between the control member and the return member and formed with an opening in which the first and the second engagement portions are inserted and which allows relative movement of the control member and the lancet holder in the back and forth direction.

Preferably, the lancet holder includes a contact portion which comes into contact with a rear end of the return member to compress the return member when the lancet advances and pricks a lancing target portion, and the compression of the return member by the contact portion generates a force to retreat the lancet holder.

Preferably, the contact portion is provided at a position deviated from the second engagement portion and the rear stopper in a direction crossing the back and forth direction to avoid contact with the second engagement portion and the rear stopper.

Preferably, the housing includes a housing body and a cap to be mounted to a front end of the housing body, and the cap is formed with the above-described opening. When the lancet detachment operation is performed, the cap is pushed by the control member to be detached from the housing body before the lancet is pushed out of the lancet holder.

Preferably, the cap is connected to the housing body via a connector so as not to drop when detached from the housing body.

Other features and advantages of the present invention will become more apparent from description of embodiments of the present invention given below with reference to the accompanying drawings.

BRIEF DESCRIPTION OF THE DRAWINGS

FIG. 2 is an exploded perspective view of the lancing device illustrated in FIG. 1.

FIG. 3A is a sectional view illustrating the lancing device of FIG. 1 in an unused state, whereas

FIGS. 4A and 4B are perspective views of the lancing device shown in FIG. 3A, with the illustration of a housing omitted.

FIG. 6A is a sectional view of a principal portion in a state in which a lancet is pushed into the lancing device of FIG. 1 and located at a predetermined retreated position, whereas FIG. 6B is a plan view schematically illustrating a principal portion of FIG. 6A.

FIGS. 7A and 7B are perspective views illustrating the lancing device of FIG. 6A, with the illustration of a housing omitted.

FIG. 8A is a sectional view illustrating a state in which a lancet is advanced toward a lancing target portion from the state illustrated in FIG. 6A, whereas FIG. 8B is a plan view schematically illustrating a principal portion of FIG. 8A.

FIG. 9A is a sectional view illustrating a lancet retreat operation performed by handling a control member in the lancing device of FIG. 1, whereas FIG. 9B is a plan view schematically illustrating a principal portion of FIG. 9A.

FIG. 10A is a sectional view illustrating the detachment of a used lancet from the lancing device of FIG. 1, whereas FIG. 10B is a plan view schematically illustrating a principal portion of FIG. 10A.

DETAILED DESCRIPTION OF THE INVENTION

Figure 1:
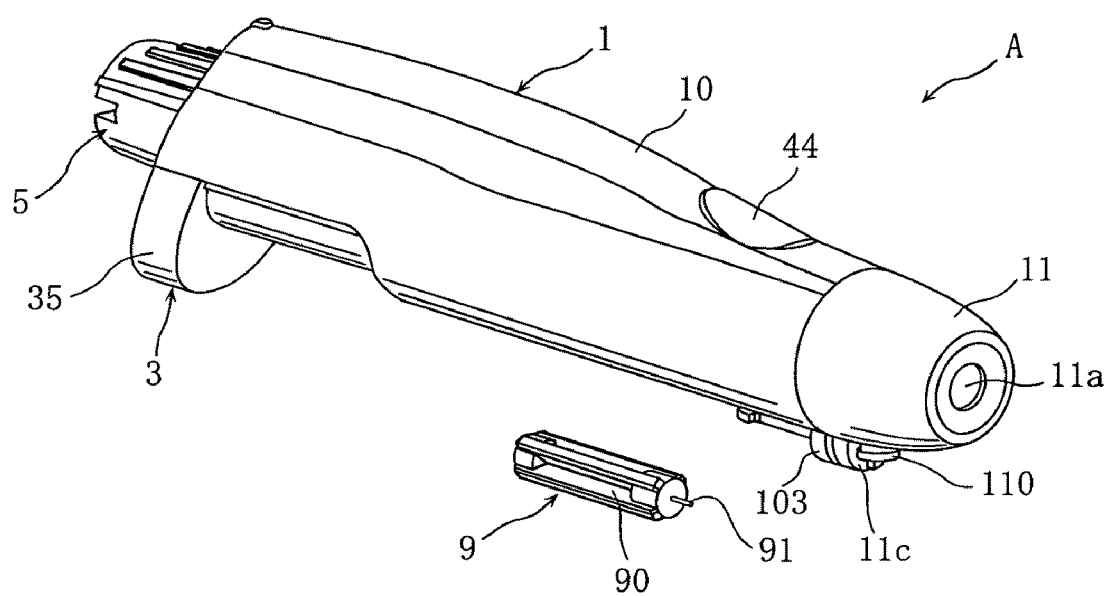
FIG. 1 is an external view illustrating an example of lancing device according to the present invention.

Preferred embodiments of the present invention are described below in detail with reference to the accompanying drawings.

FIGS. 1 to 11 illustrate an example of lancing device according to the present invention and its related structure. As clearly illustrated in FIG. 1, in the lancing device A of this embodiment, a control portion 35, an advance button 44 and a lancing depth adjustment dial 5 are provided outside the housing 1. A lancet 9 is made up of a body 90 made of a resin and a needle 91 made of a metal and attached to an end of the body. As will be described later, the lancet is used as arranged in the housing 1. The lancing device A is used to prick skin S of a finger or an arm with the needle 91 of the lancet 9 (see also FIG. 8A) to take blood from the skin S for measurement of the glucose level in the blood.

As clearly illustrated in FIG. 2, in addition to the housing 1, the lancing device A includes an auxiliary member 4, a lancet holder 2, a control member 3, an advance spring 8 and a return member 7. As will be described later, in the lancing device A, with the lancet 9 held by the lancet holder 2, the lancet holder 2 is retreated in the direction indicated by the arrow N2. In this state, when the advance button 44 is pressed, the lancet holder 2 quickly advances in the direction indicated by the arrow N1 due to the resilient force of the advance spring 8 so that the needle 91 of the lancet 9 pricks the skin S of the user. The control member 3 is used for an operation to retreat the lancet holder 2 and for an operation to detach the lancet 9 from the lancet holder 2 after the lancing operation is finished. After movement of the control member 3 or the lancet holder 2, the return member 7 functions to return these members to their original wait positions. The structure of the lancing device A is described below in more detail.

Figure 5:
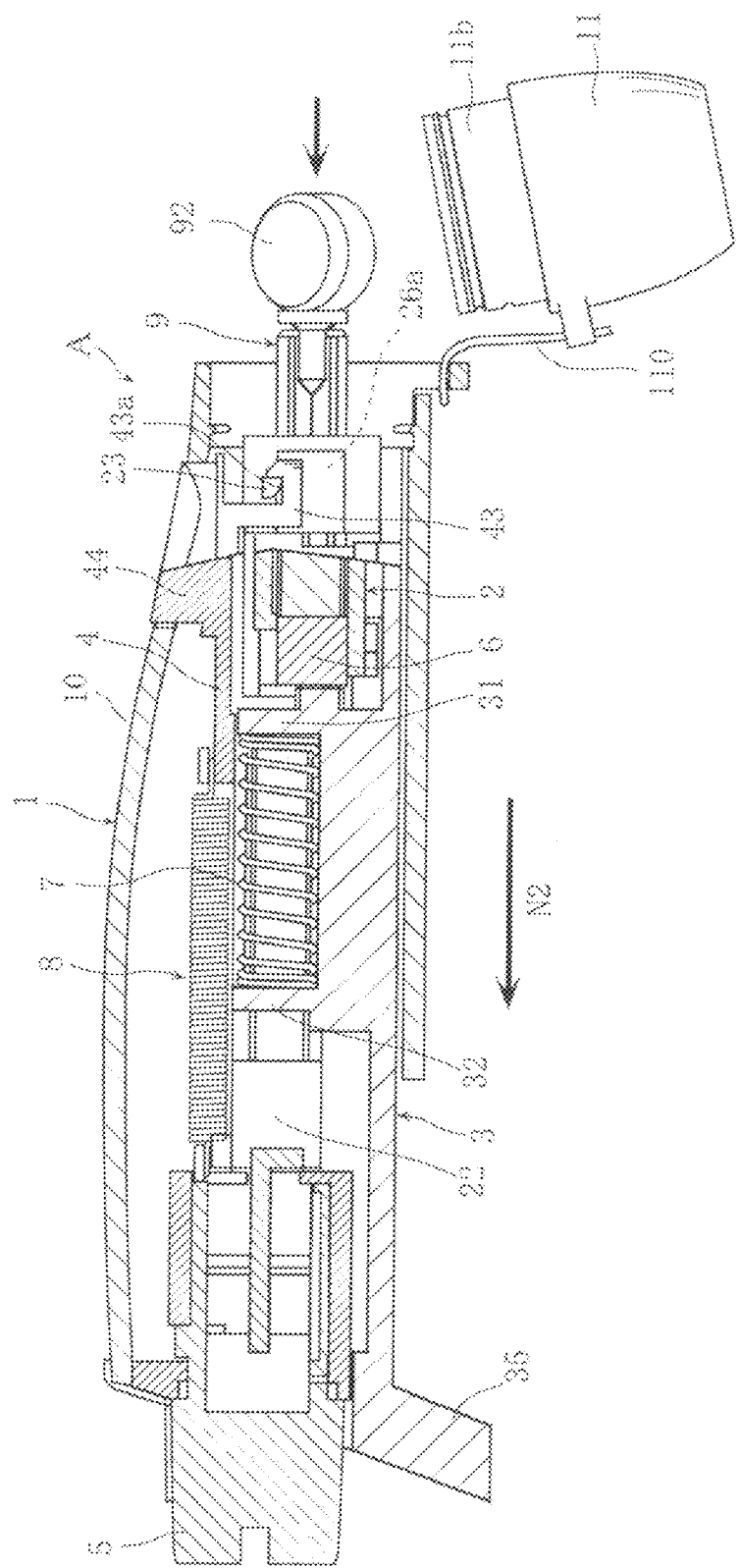
FIG. 5 is a sectional view illustrating the lancing device of FIG. 1 in a state before a lancet is mounted.

The housing 1 includes a generally cylindrical housing body 10, and a cap 11 to be mounted to the front end of the housing body 10. The cap 11 is formed with an opening 11a. The housing body 10 is formed with a projection 104 at the inner circumference of the front end opening 102. The cap 11 includes a cylindrical portion 11b at the base end, and the outer circumference surface of the cylindrical portion is formed with a recess 11d. When the cylindrical portion 11b of the cap 11 is fit into the opening 102, the projection 104 and the recess 11d engage with each other, whereby easy detachment of the cap 11 from the housing body 10 is prevented. The housing body 10 and the cap 11 are respectively formed with holder portions 103 and 11c for holding a connector 110 and connected to each other via the connector 110. Thus, as illustrated in FIGS. 5 and 10A, the cap 11 is prevented from dropping when detached from the housing body 10.

As illustrated in FIG. 2, the auxiliary member 4 includes the advance button 44, a pair of engagement portions 43 each provided with a notch 43a, a pair of front stoppers 41A, 41B and a pair of rear stoppers 41C, 41D. The auxiliary member 4 is arranged in the housing 1 so as not to move in the back and forth direction of the housing 1. However, of the auxiliary member 4, the portion near the front end at which the advance button 44 is provided is displaceable up and down in FIG. 2. The advance button 44 is exposed to the outside of the housing 1 through a hole 101 formed in the upper wall or side wall of the housing 1. When the advance button 44 is pressed, the paired engagement portions 43 displace downward in FIG. 2. As will be described later, when the lancet holder 2 is retreated, the paired engagement portions 43 serve to maintain the retreated state.

The return member 7 is a compression spring or a helical compression spring. Instead of a compression spring, the return member 7 can be made of a resilient material such as rubber or urethane foam. The front and rear stoppers 41A-41D of the auxiliary member 4 are downward projections, and the region 41 between the front stoppers 41A, 41B and the rear stoppers 41C, 41D is used to hold the return member 7. The front stoppers 41A and 41B are in contact with the front end 71 of the return member 7 to restrict the forward movement of the front end 71. The rear stoppers 41C and 41D are in contact with the rear end 72 of the return member 7 to restrict the backward movement of the rear end 72. In the present invention, the side surfaces of the front stoppers 41A, 41B and the side surfaces of the rear stoppers 41C, 41D may be connected to each other to have a box-like shape.

The lancet holder 2 is arranged between the auxiliary member 4 and the control member 3 and movable in the back and forth direction of the housing 1. The lancet holder 2 is formed with a hole 26a for holding the lancet 9, and a pair of projections 23. The hole 26a is provided at the front end of the lancet holder 2, and the lancet 9 can be fit into the hole 26a from the front side of the hole. When the lancet holder 2 is retreated, the paired projections 23 engage the paired engagement portions 43 to maintain the retreated state of the lancet holder 2

(see FIGS. 5 and 9A). The projections 23 and the engagement portions 43 are disengaged from each other by pressing the advance button 44.

The advance spring 8 is a tension spring and functions to advance the lancet holder 2 quickly toward the front side of the housing 1 when the advance button 44 is pressed in the state in which the lancet holder 2 is retreated. The opposite ends 81 and 82 of the advance spring 8 are held in engagement with engagement portions 45 and 24 respectively provided in the auxiliary member 4 and the lancet holder 2 (see also FIGS. 4A and 4B). Thus, when the lancet holder 2 is retreated in the direction indicated by the arrow N2 relative to the auxiliary member 4 and the housing 1, the advance spring 8 expands to be ready to exert a resilient force (see also FIGS. 6A, 7A and 7B).

Figure 11:
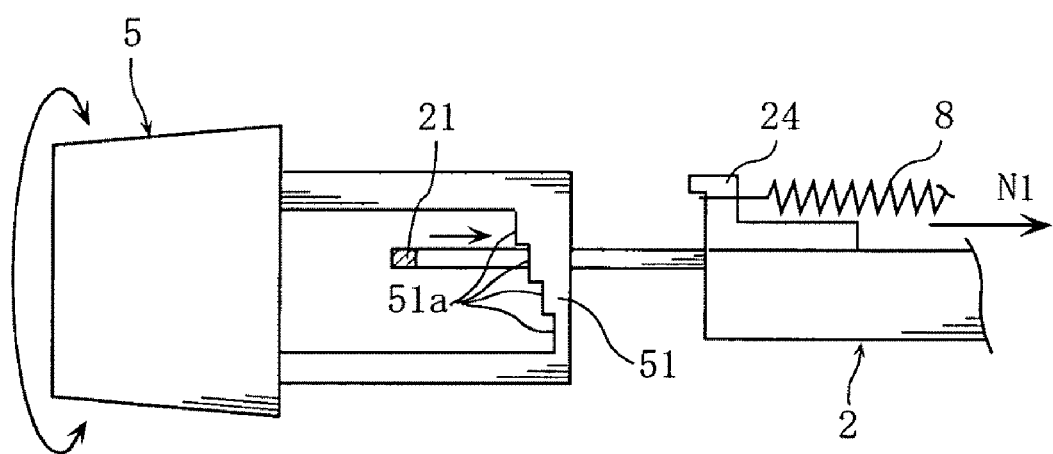
FIG. 11 is a view schematically illustrating a principal portion of a lancing depth adjustment mechanism of the lancing device illustrated in FIG. 1.
Figure 12:
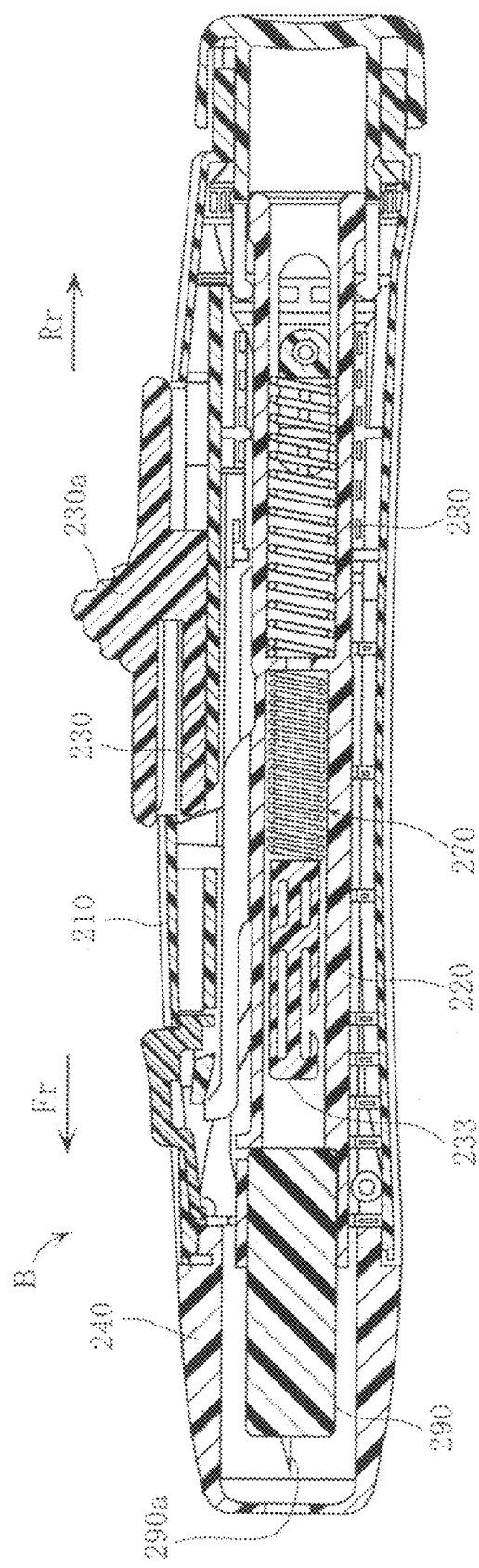
FIG. 12 is a sectional view illustrating an example of conventional device.

The lancet holder 2 includes at the rear portion a projection 21 which is engageable with a frame 51 connected to the lancing depth adjustment dial 5. Specifically, as illustrated in FIG. 11, the frame 51 is formed with a plurality of rear surface portions 51a arranged stepwise. When the lancet holder 2 is advanced, the projection 21 engages any one of the rear surface portions 51a to stop the advance movement of the lancet holder 2. By rotating the lancing depth adjustment dial 5 and thereby causing the projection 21 to engage a selected one of the rear surface portions 51a, the stroke of the lancet holder 2 is adjusted, whereby the lancing depth of the lancet 9 in the skin S is adjusted.

The control member 3 includes the control portion 35, which is in the form of a protrusion, and can be moved in the back and forth direction of the housing 1 by handling the control portion 35. By using the control member 3, a lancet retreat operation and a lancet detachment operation can be performed. In the lancet retreat operation, the control member 3 is retreated in the direction of the arrow N2 as illustrated in FIG. 9A from the state located at the wait position illustrated in FIG. 3A. By this operation, the lancet holder 2 also retreats to locate the lancet 9 at a retreated position some distance away from the opening 11a of the cap 11. In the lancet detachment operation, the control member 3 is advanced in the direction of the arrow N1 as illustrated in FIG. 10A from the state located at the wait position illustrated in FIG. 3A. By this operation, the cap 11 is detached from the housing body 10, and the lancet 9 is pushed out of the lancet holder 2. These operations are described later in detail. The operation to locate the lancet 9 at the retreated position can be performed also by pushing the lancet holder 2 using the lancet 9 without using the control member 3. This point is also described later.

As clearly illustrated in FIG. 2, the control member 3 is formed with a first and a second engagement portions 31 and 32, which are upward projections. The first and the second engagement portions 31 and 32 are inserted in the opening 28 formed in the lancet holder 2 and sandwich the return member 7 in the back and forth direction of the housing 1. Specifically, as illustrated in FIG. 3B, the first and the second engagement portions 31 and 32 are located in front of and behind the return member 8 and can come into contact with the front end 71 and the rear end 72 of the return member 7, respectively. As a means to avoid the contact of the first engagement portion 31 with the front stoppers 41A, 41B, an opening 46 is provided between the front stoppers 41A and 41B. Similarly, as a means to avoid the contact of the second engagement portion 32 with the rear stoppers 41C, 41D, an opening 47 is provided between the rear stoppers 41C and 41D. When the control member 3 moves back and forth, the first and the second engagement portions 31 and 32 pass through the openings 46 and 47.

The lancet holder 2 is formed with a protrusion 22 sticking out forward from the rear surface 28a of the inner wall of the opening 28. The protrusion 22 is provided at a position deviated from the rear stoppers 41C, 41D and the second engagement portion 32 in the width direction of the housing 1 so as not to come into contact therewith. The front end of the protrusion 22 is a contact portion 22a, which can come into contact with the rear end 72 of the return member 7. As illustrated in FIGS. 8A and 8B, when the lancet holder 2 and the lancet 9 are advanced, the contact portion 22a comes into contact with the rear end 72 of the return member 7 to compress the return member 7.

A movable member 6 for pushing out a lancet is provided in the lancet holder 2 at a position adjacent to the front end. As illustrated in FIGS. 10A and 10B, when the first and the second engagement portions 31 and 32 are advanced by the advance movement of the control member 3 in the arrow N1 direction, the movable member 6 is pushed forward by the projection 33 formed on the first engagement portion 31. As a result, the movable member 6 pushes out the lancet 9 forward from the hole 26a. Preferably, the movable member is so arranged that an appropriate frictional resistance occurs between the movable member 6 and the lancet holder 2 or frictional resistance gradually increases when the movable member 6 advances. This arrangement prevents the lancet 9 from jumping out from the hole 26a.

The control member 3 includes a cap pushing portion 34 at the front end. When the control member 3 is advanced, the cap pushing portion 34 comes into contact with and pushes the rear end surface of the cap 11 to detach the cap 11 from the housing body 10 before the lancet 9 is pushed out from the hole 26a.

The material for each part of the lancing device A is as follows. The lancing depth adjustment dial 5, the cap 11 and the lancet holder 2 are made of polycarbonate. The auxiliary member 4, the control member 3 and the movable member 6 are made of polyacetal. The housing body 10 is made of ABS resin. Each of these members may be made of other resins such as polyethylene, polypropylene or polystyrene. The connector 110 is made of e.g. thermoplastic elastomer. However, materials such as natural rubber, synthetic rubber, polycarbonate, polyethylene, polypropylene, polyacetal or polystyrene may be used instead. The needle 91 of the lancet 9 is made of e.g. stainless steel. The material for the body 90 is e.g. polyethylene, polycarbonate, polypropylene, polyacetal or polystyrene.

The use and operation of the lancing device A are described below.

Figure 3A:
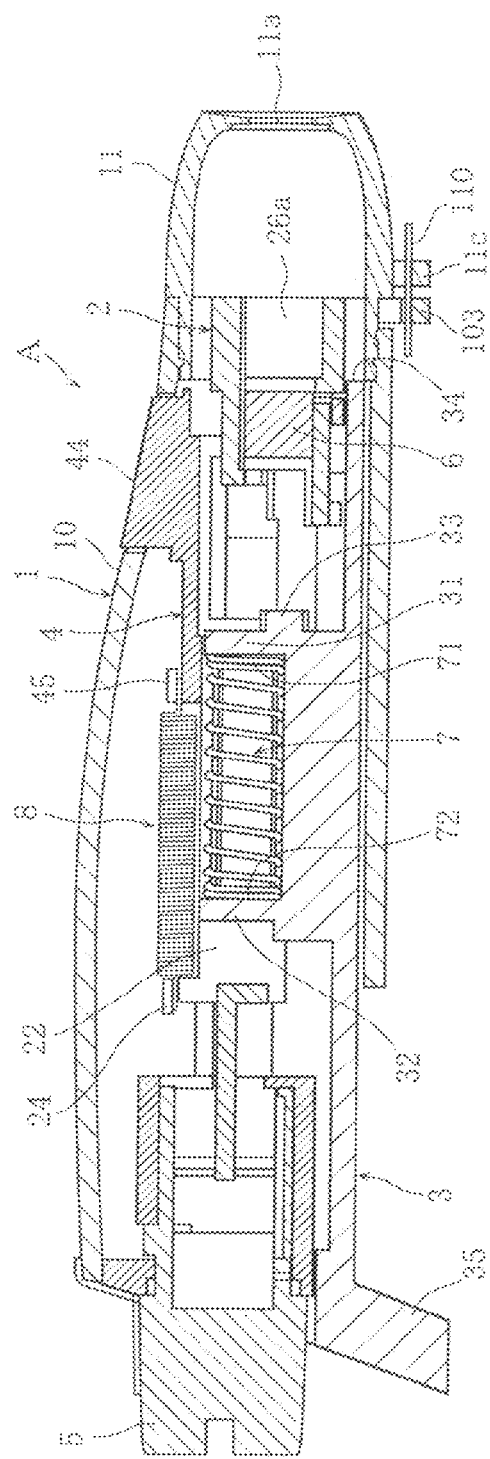
Figure 3B:
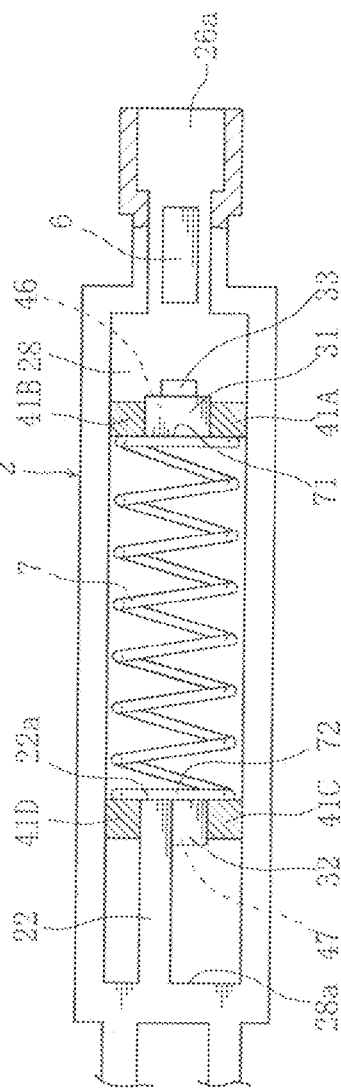
FIG. 3B is a plan view schematically illustrating a principal portion of FIG. 3A.

In an unused state illustrated in FIGS. 3A and 3B, the control member 3 is located at a predetermined wait position. In this state, the advance spring 8 is not expanded, and the return member 7 is in an uncompressed state. To use the lancing device A, a lancet 9 is set to the lancet holder 2. This operation is performed by fitting the lancet 9 into the hole 26a of the lancet holder 2, with the cap 11 detached from the housing body 10, as illustrated in FIG. 5. Preferably, a protective cap 92 for covering the needle 91 is attached to the lancet 9 in advance. In fitting the lancet 9 into the hole 26a, by pushing the lancet 9 backward in the direction indicated by the arrow N2, the lancet holder 2 is retreated in the same direction against the resilient force of the advance spring 8. Thus, in the process to mount the lancet 9, the lancet 9 can be set to the predetermined retreated position without handling the control member 3. During this process, the control member 3 is kept at the predetermined wait position.

After the above-described operation is performed, the cap 92 is removed from the lancet 9, and then the cap 11 is mounted to the housing body 10. By this, preparation for the advance movement of the lancet 9 and the lancet holder 2 is completed, as illustrated in FIG. 6A. In this state, the advance spring 8 is expanded, and the engagement of the projections 23 with the engagement portions 43 as illustrated in FIG. 5 keeps the lancet holder 2 from advancing. As illustrated in FIG. 6B, although the lancet holder 2 is retreated relative to the return member 7 and the first and the second engagement portions 31 and 32, the return member 7 is still in an uncompressed state.

When the advance button 44 is pressed in the state illustrated in FIG. 6A, the projections 23 and the engagement portions 43 disengage from each other, so that the lancet holder 2 quickly advances due to the resilient force of the advance spring 8. Thus, as illustrated in FIG. 8A, the needle 91 of the lancet 9 projects from the opening 11a of the cap 11 to prick the skin S of the user, causing bleeding from the skin S for taking of blood. As noted before, when the lancet holder 2 advances, the contact portion 22a comes into contact with the rear end 72 of the return member 7 to compress the return member 7, as illustrated in FIG. 8B. Thus, the lancet holder 2 then retreats due to the resilient force of the return member 7. Thus, the needle 91 is prevented from being left projecting from the opening 11a.

In some cases, because of the user's failure or the like, bleeding from the skin S may not be caused properly and the lancing operation may need to be performed again. To perform the lancing operation in the second time, the control member 3 is retreated in the direction of the arrow N2 by handling the control portion 35 of the control member 3, as illustrated in FIG. 9A. Specifically, when the control member is handled in this way, the second engagement portion 32 comes into contact with and pushes the rear surface 28a backward as clearly illustrated in FIG. 9B, whereby the lancet holder 2 is retreated properly. As a result, the lancet 9 is located at the predetermined retreated position, with the advance spring 8 expanded and the projections 23 and the engagement portions 43 held in engagement with each other. In this case, the first engagement portion 31 retreats and pushes the front end 71 of the return member 7 backward, so that the return member 7 is compressed. Thus, after the lancing operation is performed by pressing the advance button 44 and advancing the lancet holder 2 again, the return member 7 exerts a resilient force to push the first engagement portion 31 forward and advance the control member 3. As a result, the control member 3 automatically returns to the original wait position.

After blood is taken properly by the lancing operation described above, the lancet 9 is taken out of the housing 1. This operation is performed by advancing the control member 3 in the direction of the arrow N1 as illustrated in FIG. 10A. When the control member 3 is advanced in this way, the cap pushing portion 34 at the front end of the control member 3 comes into contact with the rear end surface of the cap 11 and pushes the cap 11 forward of the housing body 10. Since the cap 11 is connected to the housing body 10 via the connector 110, the cap 11 is prevented from dropping and being lost. Then, when the control member 3 is further advanced, as illustrated in FIG. 10B, the first engagement portion 31 pushes the rear end of the lancet 9 forward via the movable member 6. As a result, the lancet 9 is pushed out from the hole 26a of the lancet holder 2. The lancet 9 is disposed of with the needle 91 sticking in a side portion of the protective cap 92. This prevents erroneous sticking and infection.

As illustrated in FIG. 10B, in the above-described operation to push out the lancet 9, the second engagement portion 32 pushes the rear end 72 of the return member 7 to compress the return member 7. Thus, after the push-out operation of the lancet 9, the return member 7 exerts a resilient force to push the second engagement portion 32 backward and retreat the control member 3. Thus, the control member 3 automatically returns to the original wait position.

In this way, in the lancing device A, the control member 3 automatically returns to its original wait position by the use of the resilient force of the return member 7 both after the operation to retreat the control member 3 to locate the lancet 9 at the predetermined retreated position and after the operation to advance the control member 3 to detach the lancet 9. Thus, the lancing device A is convenient. The lancing device A uses the single return member 7 as a return member to automatically return the control member 3 to the original wait position. Thus, as compared with a structure in which another return spring is provided in addition to the return member 7, the number of parts of the entire device is reduced, the structure is simplified, and the size and manufacturing cost of the device are reduced. In particular, in the lancing device A, part of the lancet holder 2 is disposed between the return member 7 and the control member 3, and the first and the second engagement portions 31 and 32 of the control member 3 are designed to come into contact with the front end 71 and the rear end 72 of the return member 7 while penetrating through the opening 28 of the lancet holder 2. The arrangement of these parts in this way is space efficient and suitable for the size reduction of the lancing device A. Further, in the lancing device A, not only the lancet 9 but also the cap 11 is detached by advancing the control member 3, which is convenient.

The present invention is not limited to the foregoing embodiments. The specific structure of each part of the lancing device according to the present invention can be varied in design in many ways.

The control member of the present invention may not comprise a single member. For instance, the control member may be made up of two separate parts one of which functions to retreat the lancet holder 2 and the other one of which functions to push out the lancet 9. As noted before, the return member of the present invention may be provided by a resilient member other than a compression spring.

The invention claimed is:

1. A lancing device comprising:
   a housing including an opening at a front end thereof;
   a lancet holder for holding a lancet within the housing, the lancet holder being movable in a back and forth direction of the housing to be able to advance the lancet toward the opening from a retreated position spaced from the opening;
   a control member which is movable from a predetermined wait position in a first and a second directions, movement of the control member in the second direction from the wait position enabling a lancet retreat operation for retreating the lancet holder to locate the lancet at the retreated position, movement of the control member in the first direction from the wait position enabling a lancet detachment operation for pushing out the lancet forward of the lancet holder;
   a return member for returning the control member to the wait position after the lancet retreat operation is performed and returning the control member to the wait position after the lancet detachment operation is performed;
   a front stopper and a rear stopper provided in the housing in contact with a front end and a rear end of the return member to restrict movement of the front end and the rear end in a back and forth direction; and a first and a second engagement portions provided at the control member and positioned to sandwich the return member in the back and forth direction; wherein:

during the lancet retreat operation, the first engagement portion retreats to compress the return member between the first engagement portion and the rear stopper so that the return member pushes the first engagement portion forward after the lancet retreat operation; and during the lancet detachment operation, the second engagement portion advances to compress the return member between the second engagement portion and the front stopper so that the return member pushes the second engagement portion backward after the lancet detachment operation.

2. The lancing device according to claim 1, wherein:

one of the front stopper and the first engagement portion is formed with an opening to avoid contact with the other one, the opening having a width in a direction crossing the back and forth direction; and one of the rear stopper and the second engagement portion is formed with an opening to avoid contact with the other one, the opening having a width in a direction crossing the back and forth direction.

3. The lancing device according to claim 1, wherein:

the first and the second engagement portions are projections projecting from the control member toward the return member;

part of the lancet holder is positioned between the control member and the return member; and said part of the lancet holder is formed with an opening in which the first and the second engagement portions are inserted and which allows relative movement of the control member and the lancet holder in the back and forth direction.

4. The lancing device according to claim 1, wherein the lancet holder includes a contact portion which comes into contact with a rear end of the return member to compress the return member when the lancet advances and pricks a lancing target portion, the compression of the return member by the contact portion generating a force to retreat the lancet holder.

5. The lancing device according to claim 4, wherein the contact portion is provided at a position deviated from the second engagement portion and the rear stopper in a direction crossing the back and forth direction to avoid contact with the second engagement portion and the rear stopper.

6. The lancing device according to claim 1, wherein:

the housing includes a housing body and a cap to be mounted to a front end of the housing body, the cap being formed with said opening; and when the lancet detachment operation is performed, the cap is pushed by the control member to be detached from the housing body before the lancet is pushed out of the lancet holder.

7. The lancing device according to claim 6, wherein the cap is connected to the housing body via a connector so as not to drop when detached from the housing body.

8. The lancing device according to claim 1, wherein the return member further functions to retreat the lancet holder after the lancet has advanced and pricked a lancing target portion.

9. The lancing device according to claim 1, wherein the return member includes a resilient member.

10. The lancing device according to claim 9, wherein the resilient member is a compression spring.

* * * * *